United States Patent
Cruise et al.

(10) Patent No.: US 10,194,915 B2
(45) Date of Patent: *Feb. 5, 2019

(54) IMPLANTATION DEVICES INCLUDING HYDROGEL FILAMENTS

(71) Applicant: MicroVention, Inc., Tustin, CA (US)

(72) Inventors: Gregory M. Cruise, Rancho Santa Margarita, CA (US); Michael J. Constant, Mission Viejo, CA (US); Edward Michael Keeley, Huntington Beach, CA (US); Terrance T. Tran, Westminster, CA (US)

(73) Assignee: MicroVention, Inc., Aliso Viejo, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/272,305

(22) Filed: Sep. 21, 2016

(65) Prior Publication Data

US 2017/0007264 A1    Jan. 12, 2017

Related U.S. Application Data

(60) Continuation of application No. 13/899,357, filed on May 21, 2013, now Pat. No. 9,486,221, which is a division of application No. 12/340,544, filed on Dec. 19, 2008, now Pat. No. 8,470,035.

(60) Provisional application No. 61/016,342, filed on Dec. 21, 2007.

(51) Int. Cl.
| | | |
|---|---|---|
| *A61B 17/00* | (2006.01) |
| *A61B 17/12* | (2006.01) |
| *A61B 90/00* | (2016.01) |
| *A61K 49/04* | (2006.01) |
| *A61L 24/00* | (2006.01) |
| *A61L 24/04* | (2006.01) |
| *A61L 27/16* | (2006.01) |
| *A61L 27/18* | (2006.01) |
| *A61L 27/56* | (2006.01) |
| *A61L 31/04* | (2006.01) |
| *A61L 31/06* | (2006.01) |
| *A61L 31/14* | (2006.01) |
| *A61L 31/18* | (2006.01) |
| *C08L 39/06* | (2006.01) |
| *C08L 71/02* | (2006.01) |

(52) U.S. Cl.
CPC .. *A61B 17/12113* (2013.01); *A61B 17/12181* (2013.01); *A61B 90/39* (2016.02); *A61K 49/0404* (2013.01); *A61L 24/001* (2013.01); *A61L 24/0031* (2013.01); *A61L 24/046* (2013.01); *A61L 27/16* (2013.01); *A61L 27/18* (2013.01); *A61L 27/56* (2013.01); *A61L 31/048* (2013.01); *A61L 31/06* (2013.01); *A61L 31/146* (2013.01); *A61L 31/18* (2013.01); *A61B 2017/00004* (2013.01); *A61B 2017/1205* (2013.01); *A61B 2090/3966* (2016.02); *A61L 2430/36* (2013.01)

(58) Field of Classification Search
None
See application file for complete search history.

(56) References Cited

U.S. PATENT DOCUMENTS

| | | | |
|---|---|---|---|
| 3,709,842 A | 1/1973 | Stoy et al. |
| 3,749,085 A | 7/1973 | Wilson et al. |
| 4,020,829 A | 5/1977 | Wilson et al. |
| 4,301,803 A | 11/1981 | Handa et al. |
| 4,304,232 A | 12/1981 | Michaels |
| 4,365,621 A | 12/1982 | Brundin |
| 4,402,319 A | 9/1983 | Handa et al. |
| 4,493,329 A | 1/1985 | Crawford et al. |
| 4,509,504 A | 4/1985 | Brundin |
| 4,529,739 A | 7/1985 | Scott et al. |
| 4,551,132 A | 11/1985 | Pasztor et al. |
| 4,663,358 A | 5/1987 | Ryon et al. |
| 4,795,741 A | 1/1989 | Leshchiner et al. |
| 4,819,637 A | 4/1989 | Dormandy, Jr. et al. |
| 4,932,419 A | 6/1990 | de Toledo |
| 4,951,677 A | 8/1990 | Crowley et al. |
| 4,994,069 A | 2/1991 | Ritchart et al. |
| 5,120,349 A | 6/1992 | Stewart et al. |
| 5,122,136 A | 6/1992 | Guglielmi et al. |
| 5,129,180 A | 7/1992 | Stewart |
| 5,133,731 A | 7/1992 | Butler et al. |

(Continued)

FOREIGN PATENT DOCUMENTS

| | | |
|---|---|---|
| CA | 2551373 C | 6/2014 |
| CN | 102107025 B | 5/2014 |

(Continued)

OTHER PUBLICATIONS

Ahuja et al., Platinum coil coatings to increase thrombogenicity: a preliminary study in rabbits, AJNR, 14: 794-789 (1993).

(Continued)

*Primary Examiner* — Susan T Tran
*Assistant Examiner* — William Craigo
(74) *Attorney, Agent, or Firm* — K&L Gates LLP; Louis C. Cullman; Brian J. Novak

(57) ABSTRACT

Described are devices for implantation comprising a hydrogel filament wherein the hydrogel filament includes a low molecular weight ethylenically unsaturated macromer, an ethylenically unsaturated monomer, and a visualization agent. Methods of making and using these devices are also described.

14 Claims, No Drawings

(56) References Cited

U.S. PATENT DOCUMENTS

| | | |
|---|---|---|
| 5,147,646 A | 9/1992 | Graham |
| 5,154,705 A | 10/1992 | Fleischhacker et al. |
| 5,163,952 A | 11/1992 | Froix |
| 5,165,421 A | 11/1992 | Fleischhacker et al. |
| 5,217,484 A | 6/1993 | Marks |
| 5,226,911 A | 7/1993 | Chee et al. |
| 5,258,042 A | 11/1993 | Mehta |
| 5,304,194 A | 4/1994 | Chee et al. |
| 5,312,415 A | 5/1994 | Palermo |
| 5,350,397 A | 9/1994 | Palermo et al. |
| 5,354,290 A | 10/1994 | Gross |
| 5,373,619 A | 12/1994 | Fleischhacker et al. |
| 5,382,259 A | 1/1995 | Phelps et al. |
| 5,382,260 A | 1/1995 | Dormandy, Jr. et al. |
| 5,443,478 A | 8/1995 | Purdy |
| 5,447,727 A | 9/1995 | Graham |
| 5,449,369 A | 9/1995 | Imran |
| 5,456,693 A | 10/1995 | Conston et al. |
| 5,469,867 A | 11/1995 | Schmitt |
| 5,476,472 A | 12/1995 | Dormandy, Jr. et al. |
| 5,483,022 A | 1/1996 | Mar |
| 5,522,822 A | 6/1996 | Phelps et al. |
| 5,525,334 A | 6/1996 | Ito et al. |
| 5,536,274 A | 7/1996 | Neuss |
| 5,541,234 A | 7/1996 | Unger et al. |
| 5,549,624 A | 8/1996 | Mirigian |
| 5,573,520 A | 11/1996 | Schwartz et al. |
| 5,573,994 A | 11/1996 | Kabra et al. |
| 5,578,074 A | 11/1996 | Mirigian |
| 5,580,568 A | 12/1996 | Greff et al. |
| 5,582,610 A | 12/1996 | Grossi et al. |
| 5,582,619 A | 12/1996 | Ken |
| 5,607,417 A | 3/1997 | Batich et al. |
| 5,609,629 A | 3/1997 | Fearnot et al. |
| 5,612,050 A | 3/1997 | Rowe et al. |
| 5,624,461 A | 4/1997 | Mariant |
| 5,624,685 A | 4/1997 | Takahashi et al. |
| 5,634,936 A | 6/1997 | Linden et al. |
| 5,645,558 A | 7/1997 | Horton |
| 5,651,979 A | 7/1997 | Ron et al. |
| 5,658,308 A | 8/1997 | Snyder |
| 5,667,767 A | 9/1997 | Greff et al. |
| 5,672,634 A | 9/1997 | Tseng et al. |
| 5,678,296 A | 10/1997 | Fleischhacker et al. |
| 5,690,666 A | 11/1997 | Berenstein et al. |
| 5,690,667 A | 11/1997 | Gia |
| 5,690,671 A | 11/1997 | McGurk et al. |
| 5,695,480 A | 12/1997 | Evans et al. |
| 5,702,361 A | 12/1997 | Evans et al. |
| 5,718,711 A | 2/1998 | Berenstein et al. |
| 5,725,568 A | 3/1998 | Hastings |
| 5,749,894 A | 5/1998 | Engelson |
| 5,750,585 A | 5/1998 | Park et al. |
| 5,752,974 A | 5/1998 | Rhee et al. |
| 5,755,658 A | 5/1998 | Wallace et al. |
| 5,766,160 A | 6/1998 | Samson et al. |
| 5,766,219 A | 6/1998 | Horton |
| 5,823,198 A | 10/1998 | Jones et al. |
| 5,830,178 A | 11/1998 | Jones et al. |
| 5,843,743 A | 12/1998 | Hubbell et al. |
| 5,851,508 A | 12/1998 | Greff et al. |
| 5,853,419 A | 12/1998 | Ken et al. |
| 5,863,551 A | 1/1999 | Woerly |
| 5,883,705 A | 3/1999 | Minne et al. |
| 5,891,155 A | 4/1999 | Irie |
| 5,952,232 A | 9/1999 | Rothman |
| 5,976,162 A | 11/1999 | Doan et al. |
| 5,980,514 A | 11/1999 | Kupiecki et al. |
| 6,004,338 A | 12/1999 | Ken et al. |
| 6,004,573 A | 12/1999 | Rathi et al. |
| 6,013,084 A | 1/2000 | Ken et al. |
| 6,015,424 A | 1/2000 | Rosenbluth et al. |
| 6,017,977 A | 1/2000 | Evans et al. |
| 6,051,607 A | 4/2000 | Greff |
| 6,063,100 A | 5/2000 | Diaz et al. |
| 6,066,149 A | 5/2000 | Samson et al. |
| 6,093,199 A | 7/2000 | Brown et al. |
| 6,096,034 A | 8/2000 | Kupiecki et al. |
| 6,103,865 A | 8/2000 | Bae et al. |
| 6,136,015 A | 10/2000 | Kurz et al. |
| 6,146,373 A | 11/2000 | Cragg et al. |
| 6,159,165 A | 12/2000 | Ferrera et al. |
| 6,168,570 B1 | 1/2001 | Ferrera |
| 6,171,326 B1 | 1/2001 | Ferrera et al. |
| 6,179,857 B1 | 1/2001 | Diaz et al. |
| 6,187,024 B1 | 2/2001 | Boock et al. |
| 6,193,728 B1 | 2/2001 | Ken et al. |
| 6,201,065 B1 | 3/2001 | Pathak et al. |
| 6,231,590 B1 | 5/2001 | Slaikeu et al. |
| 6,238,403 B1 | 5/2001 | Greene, Jr. et al. |
| 6,245,090 B1 | 6/2001 | Gilson et al. |
| 6,270,748 B1 | 8/2001 | Annan et al. |
| 6,280,457 B1 | 8/2001 | Wallace et al. |
| 6,281,263 B1 | 8/2001 | Evans et al. |
| 6,287,318 B1 | 9/2001 | Villar et al. |
| 6,299,604 B1 | 10/2001 | Ragheb |
| 6,299,619 B1 | 10/2001 | Greene, Jr. et al. |
| 6,299,627 B1 | 10/2001 | Eder et al. |
| 6,303,100 B1 | 10/2001 | Ricci et al. |
| 6,312,421 B1 | 11/2001 | Boock |
| 6,333,020 B1 | 12/2001 | Wallace et al. |
| 6,335,384 B1 | 1/2002 | Evans et al. |
| 6,342,202 B1 | 1/2002 | Evans et al. |
| 6,399,886 B1 | 6/2002 | Avellanet |
| 6,423,085 B1 | 7/2002 | Murayama et al. |
| 6,425,893 B1 | 7/2002 | Guglielmi et al. |
| 6,454,738 B1 | 9/2002 | Tran et al. |
| 6,503,244 B2 | 1/2003 | Hayman |
| 6,511,468 B1 | 1/2003 | Cragg et al. |
| 6,511,472 B1 | 1/2003 | Hayman et al. |
| 6,531,111 B1 | 3/2003 | Whalen et al. |
| 6,537,569 B2 | 3/2003 | Cruise et al. |
| 6,558,367 B1 | 5/2003 | Cragg et al. |
| 6,565,551 B1 | 5/2003 | Jones et al. |
| 6,569,190 B2 | 5/2003 | Whalen et al. |
| 6,599,448 B1 | 7/2003 | Ehrhard, Jr. et al. |
| 6,602,261 B2 | 8/2003 | Greene, Jr. et al. |
| 6,605,294 B2 | 8/2003 | Sawhney |
| 6,623,450 B1 | 9/2003 | Dutta |
| 6,634,361 B1 | 10/2003 | Nikolchev et al. |
| 6,645,167 B1 | 11/2003 | Whalen et al. |
| 6,684,884 B2 | 2/2004 | Nikolchev et al. |
| 6,699,222 B1 | 3/2004 | Jones et al. |
| 6,723,108 B1 | 4/2004 | Jones et al. |
| 6,756,031 B2 | 6/2004 | Evans et al. |
| 6,759,028 B2 | 7/2004 | Wallace et al. |
| 6,849,081 B2 | 2/2005 | Sepetka et al. |
| 6,860,893 B2 | 3/2005 | Wallace et al. |
| 6,878,384 B2 | 4/2005 | Cruise et al. |
| 6,887,974 B2 | 5/2005 | Pathak et al. |
| 6,962,689 B2 | 11/2005 | Whalen et al. |
| 6,964,657 B2 | 11/2005 | Cragg et al. |
| 7,018,365 B2 | 3/2006 | Strauss et al. |
| 7,033,374 B2 | 4/2006 | Schaefer et al. |
| 7,066,904 B2 | 6/2006 | Rosenthal et al. |
| 7,070,607 B2 | 7/2006 | Murayama et al. |
| 7,083,643 B2 | 8/2006 | Whalen et al. |
| 7,138,106 B2 | 11/2006 | Evans et al. |
| 7,374,568 B2 | 5/2008 | Whalen et al. |
| 7,422,569 B2 | 9/2008 | Wilson et al. |
| 7,459,142 B2 | 12/2008 | Greff |
| 7,476,648 B1 | 1/2009 | Tabata et al. |
| 7,507,229 B2 | 3/2009 | Hewitt et al. |
| 7,507,394 B2 | 3/2009 | Whalen et al. |
| 7,976,527 B2 | 7/2011 | Cragg et al. |
| 7,988,992 B2 | 8/2011 | Omidian et al. |
| 8,066,667 B2 | 11/2011 | Hayman et al. |
| 8,235,941 B2 | 8/2012 | Hayman et al. |
| 8,377,091 B2 | 2/2013 | Cruise et al. |
| 8,454,649 B2 | 6/2013 | Cragg et al. |
| 8,486,046 B2 | 7/2013 | Hayman et al. |
| 9,011,884 B2 | 4/2015 | Constant et al. |
| 2001/0023325 A1 | 9/2001 | Ferrera |
| 2002/0026234 A1 | 2/2002 | Li et al. |

(56) References Cited

U.S. PATENT DOCUMENTS

| | | | |
|---|---|---|---|
| 2002/0042378 A1 | 4/2002 | Reich et al. | |
| 2002/0169473 A1 | 11/2002 | Sepetka et al. | |
| 2002/0176880 A1 | 11/2002 | Cruise et al. | |
| 2003/0021762 A1 | 1/2003 | Luthra et al. | |
| 2003/0077272 A1 | 4/2003 | Pathak et al. | |
| 2003/0078339 A1 | 4/2003 | Kiser et al. | |
| 2003/0086874 A1 | 5/2003 | Whalen, II et al. | |
| 2003/0100942 A1 | 5/2003 | Ken et al. | |
| 2003/0134032 A1 | 7/2003 | Chaouk | |
| 2003/0203991 A1 | 10/2003 | Schottman et al. | |
| 2003/0211083 A1 | 11/2003 | Vogel et al. | |
| 2003/0220245 A1* | 11/2003 | Hubbell | A61K 31/337 525/50 |
| 2003/0232198 A1 | 12/2003 | Lamberti et al. | |
| 2003/0232895 A1 | 12/2003 | Omidian et al. | |
| 2004/0006534 A1 | 1/2004 | Schaefer et al. | |
| 2004/0024098 A1 | 2/2004 | Mather et al. | |
| 2004/0059370 A1 | 3/2004 | Greene et al. | |
| 2004/0091543 A1 | 5/2004 | Bell et al. | |
| 2004/0098028 A1 | 5/2004 | Martinez | |
| 2004/0115164 A1* | 6/2004 | Pierce | A61K 9/0024 424/78.35 |
| 2004/0158282 A1 | 8/2004 | Jones et al. | |
| 2004/0209998 A1 | 10/2004 | De Vries | |
| 2004/0247867 A1* | 12/2004 | Chaouk | A61B 17/0057 428/364 |
| 2005/0003010 A1 | 1/2005 | Cohen et al. | |
| 2005/0008610 A1 | 1/2005 | Schwarz et al. | |
| 2005/0095428 A1 | 5/2005 | DiCarlo et al. | |
| 2005/0106119 A1 | 5/2005 | Brandom et al. | |
| 2005/0119687 A1 | 6/2005 | Dacey et al. | |
| 2005/0143484 A1 | 6/2005 | Fang et al. | |
| 2005/0171572 A1 | 8/2005 | Martinez et al. | |
| 2005/0175709 A1 | 8/2005 | Baty et al. | |
| 2005/0196426 A1* | 9/2005 | Cruise | A61K 9/0024 424/426 |
| 2005/0196449 A1 | 9/2005 | DiCarlo et al. | |
| 2005/0226935 A1 | 10/2005 | Kamath et al. | |
| 2005/0281883 A1 | 12/2005 | Daniloff et al. | |
| 2006/0052815 A1 | 3/2006 | Fitz et al. | |
| 2006/0067883 A1 | 3/2006 | Krom et al. | |
| 2006/0074370 A1 | 4/2006 | Zhou | |
| 2006/0233854 A1 | 10/2006 | Seliktar et al. | |
| 2006/0270750 A1* | 11/2006 | Almen | A61L 24/001 523/113 |
| 2007/0026039 A1 | 2/2007 | Drumheller et al. | |
| 2007/0196454 A1 | 8/2007 | Stockman et al. | |
| 2007/0202046 A1 | 8/2007 | Dave | |
| 2007/0208141 A1 | 9/2007 | Shull et al. | |
| 2007/0224234 A1 | 9/2007 | Steckel et al. | |
| 2007/0231366 A1 | 10/2007 | Sawhney et al. | |
| 2007/0237720 A1 | 10/2007 | Padilla et al. | |
| 2007/0237741 A1 | 10/2007 | Figuly et al. | |
| 2007/0248567 A1 | 10/2007 | Pathak et al. | |
| 2007/0254005 A1 | 11/2007 | Pathak et al. | |
| 2007/0288084 A1 | 12/2007 | Lee et al. | |
| 2008/0019921 A1 | 1/2008 | Zhang | |
| 2008/0038354 A1 | 2/2008 | Slager et al. | |
| 2008/0039890 A1 | 2/2008 | Matson et al. | |
| 2008/0114277 A1 | 5/2008 | Ambrosio et al. | |
| 2008/0208167 A1 | 8/2008 | Stankus | |
| 2008/0226741 A1 | 9/2008 | Richard | |
| 2008/0281352 A1 | 11/2008 | Ingenito et al. | |
| 2009/0041850 A1 | 2/2009 | Figuly | |
| 2009/0048659 A1 | 2/2009 | Weber et al. | |
| 2009/0054535 A1 | 2/2009 | Figuly et al. | |
| 2009/0081275 A1 | 3/2009 | Rolfes et al. | |
| 2009/0093550 A1 | 4/2009 | Rolfes et al. | |
| 2009/0117033 A1 | 5/2009 | O'Gara | |
| 2009/0164013 A1 | 6/2009 | Cruise et al. | |
| 2009/0181068 A1 | 7/2009 | Dunn | |
| 2009/0221731 A1 | 9/2009 | Vetrecin et al. | |
| 2009/0232869 A1 | 9/2009 | Greene | |
| 2009/0259302 A1 | 10/2009 | Trollsas et al. | |
| 2010/0010159 A1 | 1/2010 | Belcheva | |
| 2010/0023112 A1 | 1/2010 | Borck et al. | |
| 2010/0036491 A1 | 2/2010 | He et al. | |
| 2010/0042067 A1 | 2/2010 | Koehler | |
| 2010/0086678 A1 | 4/2010 | Arthur et al. | |
| 2010/0092533 A1 | 4/2010 | Stopek et al. | |
| 2010/0241160 A1 | 9/2010 | Murphy | |
| 2010/0247663 A1 | 9/2010 | Day et al. | |
| 2010/0249913 A1 | 9/2010 | Dattaa et al. | |
| 2010/0256777 A1 | 10/2010 | Dattta et al. | |
| 2010/0303804 A1 | 12/2010 | Liska et al. | |
| 2011/0008406 A1 | 1/2011 | Altman et al. | |
| 2011/0008442 A1 | 1/2011 | Zawko et al. | |
| 2011/0020236 A1 | 1/2011 | Bohmer et al. | |
| 2011/0027172 A1 | 2/2011 | Wang et al. | |
| 2011/0091549 A1 | 4/2011 | Blaskovich et al. | |
| 2011/0182998 A1 | 7/2011 | Reb et al. | |
| 2011/0184455 A1 | 7/2011 | Keeley | |
| 2011/0190813 A1 | 8/2011 | Brownlee et al. | |
| 2011/0202016 A1 | 8/2011 | Zugates et al. | |
| 2011/0212178 A1 | 9/2011 | Constant et al. | |
| 2012/0041481 A1 | 2/2012 | Daniloff et al. | |
| 2012/0083523 A1 | 4/2012 | Richard et al. | |
| 2012/0114589 A1 | 5/2012 | Rolfes-Meyering et al. | |
| 2012/0156164 A1 | 6/2012 | Park et al. | |
| 2012/0164100 A1 | 6/2012 | Li et al. | |
| 2012/0184642 A1 | 7/2012 | Bartling et al. | |
| 2012/0238644 A1 | 9/2012 | Gong et al. | |
| 2012/0244198 A1 | 9/2012 | Malmsjo et al. | |
| 2012/0283769 A1 | 11/2012 | Cruise et al. | |
| 2012/0289995 A1 | 11/2012 | Constant et al. | |
| 2013/0039848 A1 | 2/2013 | Bradbury et al. | |
| 2013/0045182 A1 | 2/2013 | Gong et al. | |
| 2013/0060230 A1 | 3/2013 | Capistron | |
| 2013/0079421 A1 | 3/2013 | Aviv et al. | |
| 2013/0108574 A1 | 5/2013 | Chevalier et al. | |
| 2013/0131716 A1 | 5/2013 | Cruise et al. | |
| 2013/0253087 A1 | 9/2013 | Cruise et al. | |
| 2014/0056806 A1 | 2/2014 | Vemengo et al. | |
| 2014/0274945 A1 | 9/2014 | Blaskovich et al. | |
| 2014/0277057 A1 | 9/2014 | Ortega et al. | |
| 2015/0190553 A1 | 7/2015 | Constant et al. | |
| 2015/0283306 A1 | 10/2015 | Constant et al. | |
| 2015/0306227 A1 | 10/2015 | Cruise et al. | |
| 2015/0306255 A1 | 10/2015 | Constant et al. | |
| 2016/0166258 A1 | 6/2016 | Cruise et al. | |
| 2016/0345978 A1 | 12/2016 | Cruise et al. | |
| 2016/0361459 A1 | 12/2016 | Baldwin | |
| 2016/0367730 A1 | 12/2016 | Constant et al. | |

FOREIGN PATENT DOCUMENTS

| | | |
|---|---|---|
| EP | 809519 B1 | 12/1997 |
| EP | 0809519 B2 * | 9/2002 |
| EP | 1599258 B1 | 8/2008 |
| EP | 1601392 B1 | 4/2009 |
| WO | 1991/004732 A1 | 9/1990 |
| WO | 1991/016057 A | 10/1991 |
| WO | 1994/003155 A1 | 2/1994 |
| WO | 1997/022365 A1 | 6/1997 |
| WO | 1997/026939 A1 | 7/1997 |
| WO | 1997/027888 A1 | 8/1997 |
| WO | 1998/001421 A1 | 1/1998 |
| WO | 1998/043615 A1 | 10/1998 |
| WO | 1998/055103 A1 | 12/1998 |
| WO | 1999/023954 A1 | 5/1999 |
| WO | 1999/044538 A1 | 9/1999 |
| WO | 1999/056783 A1 | 11/1999 |
| WO | 1999/065401 A1 | 12/1999 |
| WO | 2000/027445 A1 | 5/2000 |
| WO | 2000/038651 A1 | 7/2000 |
| WO | 2000/074577 A1 | 12/2000 |
| WO | 2001/068720 A1 | 9/2001 |
| WO | 2002/005731 A1 | 1/2002 |
| WO | 2002/096302 A1 | 12/2002 |
| WO | 2003/043552 A1 | 5/2003 |
| WO | 2005/032337 A2 | 4/2005 |
| WO | 2007/016371 A2 | 2/2007 |
| WO | 2007/147145 A2 | 12/2007 |

(56) References Cited

FOREIGN PATENT DOCUMENTS

| WO | 2000/078846 A1 | 12/2008 |
| WO | 2009/086208 A2 | 7/2009 |
| WO | 2011/038291 A1 | 3/2011 |
| WO | 2011/053555 A1 | 5/2011 |
| WO | 2012/039602 A1 | 3/2012 |
| WO | 2012/120138 A1 | 9/2012 |
| WO | 2012/145431 A3 | 10/2012 |
| WO | 2012/171478 A1 | 12/2012 |
| WO | 2013/158781 | 10/2013 |
| WO | 2015/153996 A1 | 10/2015 |
| WO | 2015/167751 A1 | 11/2015 |
| WO | 2015/167752 A1 | 11/2015 |
| WO | 2016/201250 A1 | 12/2016 |

OTHER PUBLICATIONS

Almany, Biomaterials, 26, 2005, 2467-2477, Biosynthetic hydrogel scaffolds made from fibrinogen and polyethylene glycol for 3D cell cultures.

Carelli V. et al., "Silicone microspheres for pH-controlled gastrointestinal drug delivery," 1999, International Journal of Pharmaceutics, V179, p. 73-83.

Chirila et al., Poly(2-hydroxyethyl metharcrylate) sponges ans implant materials: in vivo and in vitro evaluation of cellular invasion. Biomaterials, 14(1):26-38 (1993).

Constant et al., Preparation, Characterization, and Evaluation of Radiopaque Hydrogel Filaments for Endovascular Embolization. Journal of Biomedical Materials Research Part B: Applied Biomaterials, vol. 89B, No. 2, pp. 306-313 (2008).

Edleman et al., Controlled and modulated release of basic fibroblast growth factor. Biomaterials, vol. 12, pp. 619-626 (1991).

Elbert et al., Conjugate addition reactions combined with free-radical cross-linking for the design of materials for tissue engineering. Biomacromolecules, (2): 430-441 (2001).

European Search Opinion for EP Application No. 10819570 dated Mar. 31, 2014.

European Search Opinion for EP Application No. 10827370 dated Apr. 1, 2014.

Graves et al., Endovascular occlusion of the carotid or vertebral artery with temporary proximal flow arrest and mircocoils: clinical results. AJNR Am. J. Neuroradiol., vol. 18, pp. 1201-1206 (1997).

Hoekstra, D., Hyaluronan-modified surfaces for medical devices. Medical Device & Diagnostic Industry, pp. 48-56 (1999).

Hogg et al., Interaction of platelet-derived growth factor with thrombospondin 1. Biochem. J. 326, pp. 709-716 (1997).

Horak et al., Hydrogels in endovascular embolization. II. Clinical use of spherical particles. Biomaterials, 7(6): 467-470 (1986).

Horak et al., New radiopaque polyHEMA-based hydrogel particles. J. Biomed. Matter Res., 34(2): 183-188 (1997).

Huang, et al., "Synthesis and Characterization of Self-Assembling Block Copolymers Containing Adhesive Molecules," Polymer Preprints, vol. 42, No. 2, 2001, pp. 147-148.

International Search Report dated Dec. 17, 2010 for International Patent Application No. PCT/US2010/053972.

International Search Report dated Feb. 5, 2009 for International Patent Application No. PCT/US2007/071395.

International Search Report dated Aug. 14, 2013 for International PCT Application No. PCT/US2013/037007 filed on Apr. 17, 2013.

International Search Report and Written Opinion dated Jun. 29, 2015 for International Application No. PCT/US2015/024289 filed on Apr. 3, 2015.

International Search Report and Written Opinion dated Jun. 29, 2015 for International Application No. PCT/US2015/024290 filed on Apr. 3, 2015.

International Search Report and Written Opinion dated Jul. 14, 2015 for International Application No. PCT/US2015/024284 filed on Apr. 3, 2015.

Kim, Drug release from pH-sensitive interpenetrating polymer networks hydrogel based on poly (ethylene glycol) Macromer and Poly (acrylic acid) prepared by UV Cured Method, ArchPharmRes, vol. 19(1), 1996, p. 18-22.

Klier, Self Associating Networks of Poly(methacrylic acid g-ethylene glycol) Marcomolecules 1990, vol. 23, 1990, p. 4944-4949.

Larsen et al., Hylan gel composition for percutaneous embolization. Journal of Biomedical Materials Research, vol. 25, Issue 6, pp. 699-710 (1991).

Latchaw et al., Polyvinyl foam embolization of vascular and neoplastic lesions of the head, neck, and spine. Radiology, 131: 669-679 (1979).

Li, Jian et al., Preparation of PEG/Aac copolymerric hydrogel and study of pH-sensitivity. Chemistry World, Issue 1, pp. 20-23 (2005).

Mellott, Michael B. et al., Release of protein from highly cross-linked hydrogels of poly(ethylene glycol) diacrylate fabricated by UV polymerization. Biomaterials, 22(2001) 929-941.

Murayama et al., Cellular responses of bioabsorbable polymeric material and guglielmi detachable coil in experimental aneurysms. Stroke, pp. 1120-1128 (2002).

Persidis, A., Tissue engineering. Nature Biotechnology, 17, pp. 508-510 (1999).

Schmutz et al., Embolization of cerebral arteriovenous malformations with silk: histopathologic changes and hemorrhagic complications. AJNR Am. J. Neuroradiol., vol. 18, pp. 1233-1237 (1997).

Schoenmakers, The effect of the linker on the hydrolysis rate of drug-linked ester bonds, J. Cont. Rel., 95, 2004, pp. 291-300.

Supplementary European Search Report for EP Application No. 10819570 dated Mar. 31, 2014.

Supplementary European Search Report for EP Application No. 10827370 dated Apr. 1, 2014.

Vinuela et al., Guglielmi detachable coil embolization of acute intracranial aneurysm: perioperative anatomical and clinical outcome in 403 patients. J. Neurosurg., vol. 86, pp. 475-482 (1997).

Woerly et al., Intracerebral implantation of hydrogel-coupled adhesion peptides: tissue reaction. Journal of Neural Transplantation & Plasticity, vol. 5, No. 4, pp. 245-255 (1995).

Written Opinion dated Aug. 14, 2013 for International PCT Application No. PCT/US2013/037007 filed on Apr. 17, 2013.

Zollikofer et al., A combination of stainless steel coil and compressed ivalon: a new technique for embolization of larger arteries and arteriovenous fistulas. Radiology, 138: 229-231 (1981).

Zollikofer et al., Therapeutic blockade of arteries using compressed invalon. Radiology, 136: 635-640 (1980).

Son et al., Preparation of properties of PEG-modified PHEMA hydrogel and the morphological effect. Macromolecular Research, vol. 14, No. 3, pp. 394-399 (2006).

U.S. Appl. No. 15/236,135, filed Aug. 12, 2016.

International PCT Application PCT/US2016/036924 filed on Jun. 10, 2016.

U.S. Appl. No. 15/252,089, filed Aug. 30, 2016.

U.S. Appl. No. 15/179,212, filed Jun. 10, 2016.

International Search Report and Written Opinion dated Sep. 23, 2016 for International Application No. PCT/US2016/036924 filed on Jun. 10, 2016.

Supplementary European Search Report for EP Application No. 15785350 dated Nov. 13, 2017.

U.S. Appl. No. 15/635,046, filed Jun. 27, 2017.

U.S. Appl. No. 15/847,745, filed Dec. 19, 2017.

* cited by examiner

IMPLANTATION DEVICES INCLUDING HYDROGEL FILAMENTS

CROSS REFERENCE TO RELATED APPLICATIONS

This application is a continuation patent application of U.S. patent application Ser. No. 13/899,357, filed May 21, 2013, which is a divisional patent application of U.S. patent application Ser. No. 12/340,544, filed Dec. 19, 2008, now U.S. Pat. No. 8,470,035, which claims the benefit of U.S. Provisional Application Ser. No. 61/016,342, filed Dec. 21, 2007, the disclosures each of which are incorporated herein by reference in their entirety.

FIELD OF THE INVENTION

The present invention relates generally to medical treatment apparatus and methods, more particularly, hydrogel filaments visible under x-ray fluoroscopy and magnetic resonance, and methods for use of such materials in biomedical treatment.

BACKGROUND

Presently, for patients suffering from cerebral and/or peripheral vascular disease, an interventional neuroradiologist/neurosurgeon has three main embolic device choices: platinum coils, hydrogel/platinum coils, or degradable polymer/platinum coils. All three types of coils are deployed into aneurysms and have advantages and disadvantages associated with them. Platinum coils are easy to deploy through standard microcatheters, are available in wide ranges of softness, and are best suited for aneurysms with small sizes or necks. Hydrogel/platinum coils are also easy to deploy through standard microcatheters. Although hydrogel/platinum coils are relatively stiffer than platinum coils and can be challenging to deploy inside aneurysms, they give acceptable results in a broader range of sac and neck sizes. Degradable polymer/platinum coils are easily tracked and deployed into aneurysm sacs; however, they only give acceptable results in aneurysms with small sizes or necks.

Despite the three coil varieties, there exists an unmet clinical need for embolic devices that deploy easily into aneurysm sacs (like platinum coils) and result in durable occlusion in a wide variety of aneurysm sizes (like hydrogel/platinum coils). Among the benefits of the apparatus and methods of the present description is a device that tracks through a microcatheter with less friction than a platinum coil, deploys in the aneurysm sac like the softest platinum coil on the market, expands like the hydrogel/platinum coils, and provides durable occlusion of the aneurysm sac, while permitting the interventional neuroradiologist/neurosurgeon, or surgeon, to use standard microcatheters and other associated equipment.

The improved durability of hydrogel/platinum coils is believed to be a result of the increased volumetric filling of the aneurysm sac and the resulting increase in stability of the coil mass. A current version of the hydrogel/platinum coil has an overcoil which limits the expansion of the hydrogel. In preclinical models, while current overcoiled hydrogel/platinum coils provide better results than platinum coils, it is believed that a non-overcoiled hydrogel device would be less stiff than current overcoiled versions. The present description provides an embolic device that is capable of providing increased volumetric filling, more so than both platinum coils and overcoiled hydrogel/platinum coils, with less stiffness than overcoiled hydrogel/platinum coils.

In large and giant aneurysms, inflammatory complications can occur, presumably due to the large amount of thrombus formation and organization. It is believed that with the increased volumetric filling of the aneurysm sac provided by the hydrogel, decreased thrombus formation and organization occurs and presumably fewer inflammatory complications result. The present description provides an embolic device which could reduce inflammatory complications.

An uncommon, but potentially dangerous, complication occurs when a coil gets interlocked within the winds of the coil itself. In this case, one can neither push nor pull the coil while keeping the device intact within the aneurysm site. The only option is to pull back and unwind the coil from the aneurysm site to the groin. The potentially dangerous result is a stretched coil. Although stretch resistant coils have been developed, this complication has not been eliminated, and still poses a dangerous threat to a patient. It is believed that the device of the present description eliminates this complication altogether.

SUMMARY

Described herein are apparatuses, compositions, systems and associated methods to occlude structures and malformations in body lumens with hydrogel filaments with delayed controlled rates of expansion including one or more visualization agents permitting the repositioning of the device once inside the structure or malformation. The structures and malformations can be a result of any number of cerebral and/or peripheral diseases. Generally, the controlled rate of expansion is imparted through the incorporation of ethylenically unsaturated monomers with ionizable functional groups, (e.g. amines, carboxylic acids). For example, if acrylic acid is incorporated into the cross-linked polymeric network, the hydrogel is then incubated in a low pH solution to protonate the carboxylic acids. After the excess low pH solution has been rinsed away and the hydrogel dried, the hydrogel can be introduced through a microcatheter filled with blood or saline at physiological pH. The hydrogel cannot and will not expand until the carboxylic acid groups deprotonate. Conversely, if an amine-containing monomer is incorporated into the cross-linked network, the hydrogel is incubated in a high pH solution to deprotonate amines. After the excess high pH solution has been rinsed away and the hydrogel dried, the hydrogel can be introduced through a microcatheter filled with blood or saline at physiological pH. The hydrogel cannot and will not expand until the amine groups protonate.

In one embodiment described herein is a device for implantation comprising a difunctional, low molecular weight ethylenically unsaturated shapeable macromer; an ethylenically unsaturated monomer; and a visualization agent, wherein the device contains no support members. In one embodiment, the support members are metallic.

In one embodiment, the macromer has a molecular weight of about 100 grams/mole to about 5000 grams/mole. In another embodiment, the hydrogel is environmentally-responsive. In yet another embodiment, the ethylenically unsaturated monomer comprises one or more ionizable functional groups.

In one embodiment, the macromer comprises polyethylene glycol, propylene glycol, poly(tetramethylene oxide), poly(ethylene glycol) diacrylamide, poly(ethylene glycol) diacrylate, poly(ethylene glycol) dimethacrylate, derivatives thereof, or combinations thereof. In another embodiment, the ethylenically unsaturated monomer comprises N,N'-methylenebisacrylamide, N-vinyl pyrrolidinone, 2-hydroxyethyl methacrylate, derivatives thereof, or combinations thereof.

In one embodiment, the visualization agents include radiopaque elements comprising an aromatic ring having a single unsaturation point and at least one iodine atom, tantalum, barium, salts thereof, or combinations thereof. In one embodiment, the visualization agent an aromatic ring having a single unsaturation point and two iodine atoms. In one embodiment, the visualization agent comprises gadolinium or iron oxide to impart visibility under magnetic resonance imaging.

In one embodiment, the ethylenically unsaturated monomer and the visualization agent comprise 2,4,6-triiodophenyl penta-4-enoate, 5-acrylamido-2,4,6-triiodo-n,n'-bis-(2,3 dihydroxypropyl) isophthalamide, derivatives thereof, or combinations thereof.

In one embodiment, the polymerization of the macromer and the monomer is initiated by N,N,N',N'-tetramethylethylenediamine, ammonium persulfate, azobisisobutyronitrile, benzoyl peroxides, 2,2'-azobis(2-methylpropionamidine) dihydrochloride, derivatives thereof, or combinations thereof.

In one embodiment, the ionizable functional groups comprise acidic groups or basic groups. In one embodiment, the basic group comprises amine groups, derivatives thereof, or combinations thereof. In another embodiment, the acidic groups comprise a carboxylic acid, derivatives thereof, or combinations thereof.

In one embodiment, the hydrogel is substantially free of acrylamide. In another embodiment, the hydrogel is substantially non-bioresorbable. In another embodiment, the hydrogel is bioresorbable.

One embodiment described herein is a method for preparing a device for implantation in an animal comprising: a) combining a difunctional, low molecular weight ethylenically unsaturated shapeable macromer; an ethylenically unsaturated monomer; a visualization agent, and a solvent to prepare a prepolymer solution; and b) treating the prepolymer solution to prepare a hydrogel that is expansible at physiological conditions.

In one embodiment of the method, the solvent comprises water, dichloromethane, acetone, isopropyl alcohol, ethanol, or combinations thereof. In another embodiment, the difunctional, low molecular weight ethylenically unsaturated shapeable macromer has a molecular weight of about 100 grams/mole to about 5000 grams/mole. In yet another embodiment, the ethylenically unsaturated monomer comprises ionizable functional groups.

In one embodiment of the method, solvent comprises about 20% w/w to about 80% w/w of the prepolymer solution. In another embodiment, the monomer comprises about 40% to about 80% by weight of the prepolymer solution.

In one embodiment, the method further comprises the step of adding a second an ethylenically unsaturated monomer to the prepolymer solution.

In one embodiment of the method, the ionizable functional groups comprise basic groups and the treating step comprises de-protonating the basic groups at pHs greater than the pKa or protonating the basic groups at pHs less than the pKa of the basic groups. In another embodiment of the method, the ionizable functional groups comprise acidic groups and the treating step comprises protonating the acidic groups at pHs less than the pKa or de-protonating the acidic groups at pHs greater than the pKa of said acidic groups.

In another embodiment, a device is described for implantation comprising: a difunctional, low molecular weight ethylenically unsaturated shapeable macromer with a molecular weight of about 100 grams/mole to about 5000 grams/mole; an ethylenically unsaturated monomer; and a visualization agent, wherein the device contains no metallic support members.

DETAILED DESCRIPTION

Described herein are apparatuses, compositions, systems and associated methods for occluding structures and malformations resulting from one or more cerebral and/or peripheral vascular diseases. Hydrogel filaments comprising one or more visualization agents having delayed, controlled rates of expansion are used to treat these structures and malformations, thereby permitting the repositioning of the device once inside the structure or malformation. Further, the hydrogel filaments including one or more visualization agents, for example radiopaque elements or fillers, with controlled rates of expansion give a surgeon a sufficient amount of time to properly position the filament without the need to rush as a result of immediate filament expansion.

Generally, the controlled rate of expansion of the hydrogel filaments is imparted through the incorporation of ethylenically unsaturated monomers with ionizable functional groups, (e.g. acidic or basic groups). For example, if acrylic acid is incorporated into the cross-linked polymeric network, the hydrogel is incubated in a low pH solution to protonate acidic, carboxylic acids. After the excess low pH solution has been rinsed away and the hydrogel dried, the hydrogel can be introduced through a microcatheter filled with blood or saline at physiological pH. The hydrogel cannot and will not expand until the carboxylic acid groups deprotonate. Conversely, if a basic, amine containing monomer is incorporated into the cross-linked network, the hydrogel is incubated in a high pH solution to deprotonate amines. After the excess high pH solution has been rinsed away and the hydrogel dried, the hydrogel can be introduced through a microcatheter filled with blood or saline at physiological pH. The hydrogel cannot and will not expand until the amine groups are protonated.

In one embodiment, whether acidic or basic groups are utilized on the monomeric species according to the present description, the devices described herein are expansible at physiological conditions. Physiological condition as used herein means a condition having at least one environmental characteristic found within or on the human body. Such characteristics include isotonic environment, pH buffered environment, aqueous environment, a pH of about 7, or combinations thereof and can be found in, for example, an isotonic solution, water, blood, spinal fluid, plasma, serum, vitreous humor or urine.

In one embodiment generally described herein are devices for implantation comprising a difunctional, low molecular weight ethylenically unsaturated shapeable macromer; an ethylenically unsaturated monomer; and a visualization element, wherein the device contains no support members. In one embodiment, the device contains one or more support members, but those support members are not metallic. Non-metallic support members can be polymeric. In one embodiment, the devices have one or more non-radiopaque or visualizable support members. In some embodiments, support members are not needed in the devices described herein to control expansion of the hydrogel, and as such, they are not incorporated into the apparatus and systems described herein.

Further, the absence of metallic support members from the devices described herein allow for better resolution under various imaging procedures. Metallic support members, for example, can distort the imaging of a device by producing flares or reflections from the metallic support members within the image. As such, providing a device with no metallic support members, but including one or more visualization agents, such as radiopaque elements or fillers, as taught herein allows one skilled in the art to attain a more precise and accurate image of the device both during and after implantation. Such devices with no metallic support members may include support members not visible to imaging techniques, for example polymeric support members.

In another embodiment described herein is a method for preparing a device for implantation in an animal comprising the steps of combining a difunctional, low molecular weight ethylenically unsaturated shapeable macromer; an ethylenically unsaturated monomer; a visualization element, and a solvent to prepare a prepolymer solution; and treating the prepolymer solution to prepare hydrogel that is expansible at physiological conditions.

Generally, the prepolymer solution is comprised of a solvent, a difunctional, low molecular weight ethylenically unsaturated macromer, an ethylenically unsaturated monomer with one or more visualization agents, an ionizable ethylenically unsaturated monomer, one or more optional ethylenically unsaturated monomers with visualization agents either with or without radiopacity, and an optional porosigen. Alternatively, the prepolymer solution is comprised of a solvent, a difunctional ethylenically unsaturated macromer, optional ethylenically unsaturated monomer or monomers, optional cross-linkers, and one or more visualization agents, such as radiopaque elements or fillers, which include, but are not limited to, barium, tantalum, platinum, and gold.

The solvent in the prepolymer solution serves to completely dissolve of all macromers and monomers within the prepolymer solution. If a liquid monomer (e.g. 2-hydroxyethyl methacrylate) is used, a solvent may not be necessary. The solvent, if necessary, is selected based on the solubility of the macromers and monomers. Preferred solvents are isopropyl alcohol (IPA, isopropanol), ethanol, water, dichloromethane, and acetone; however, a number of other solvents could be utilized and are know to those skilled in the art. Preferred solvent concentrations range from about 20% w/w to about 80% w/w of the prepolymer solution, more preferably about 40% w/w to about 60% w/w. In one preferred embodiment, the solvent concentration is about 33% w/w of the prepolymer solution.

The difunctional low molecular weight ethylenically unsaturated shapeable macromer serves to cross-link the polymer chains during polymerization and impart flexibility to the resulting polymer. Such macromers include at least one ethylenically unsaturated group and two functional sites. In one embodiment, at least one ethylenically unsaturated group can be one of the functional sites, or can be both functional sites. In one embodiment, the macromers described herein have a low molecular weight. The macromers described herein have a molecular weight ranging from about 100 g/mol to about 5,000 g/mole, or about 200 g/mole to about 2,500 g/mole, more preferably about 400 g/mole to about 1,000 g/mole. A preferred macromer is poly(ethylene glycol) diacrylamide because of its biocompatibility and solubility in a wide variety of solvents. If degradation of the resulting polymer is desired, a preferred macromer is poly(ethylene glycol) diacrylate. Alternatively, more hydrophobic macromers such as the polyethers poly(propylene glycol) and poly(tetramethylene oxide) or derivatives of polyolefins such as poly(ethylene) are suitable. Other suitable macromers include polyethylene glycol, propylene glycol, and poly(ethylene glycol) dimethacrylate.

"Ethylenically unsaturated" as used herein generally describes a compound with a group such as, but not limited to, vinyl, acrylate, methacrylate, or acrylamide groups including derivatives thereof or combinations thereof.

A "shapeable" macromer is used herein to describe the relative rigidity of the macromer and its ability to hold a particular shape. For example, a shapeable macromer according to the present description can be formed using a device such as a mandrel and can hold the resulting shape for implantation.

The ethylenically unsaturated monomers with one or more visualization agents serve to impart visualization of the resulting polymer under the appropriate visualization method. In one embodiment, ethylenically unsaturated monomers comprise radiopaque elements or radiopaque elements alone which serve to impart radiopacity to the resulting polymer. Aromatic rings with single unsaturations and one or more iodine atom are preferred ethylenically unsaturated monomers with radiopaque elements. Examples include 2,4,6-triiodophenyl penta-4-enoate and 5-acrylamido-2,4,6-triiodo-n,n'-bis-(2,3 dihydroxypropyl) isophthalamide. Preferred concentrations of the unsaturated monomer with radiopaque elements range from about 40% w/w to about 80% w/w of the prepolymer solution, more preferably about 40% w/w to about 60% w/w of the prepolymer solution. Alternatively, radiopaque elements or fillers such as tantalum, barium or salts thereof can be incorporated into the prepolymer solution either in place of the radiopaque elements or in addition to them. Radiopaque filler loadings range from about 40% w/w to about 60% w/w of the resulting polymer.

"Visulaization agent" as used herein refers to any element that is added to or encompassed within the devices described herein that impart a means of visualizing the device either during or after implantation. Methods of visualization include, but are not limited to, x-rays, ultrasound, fluoroscopy, infrared radiation, ultraviolet light methods, magnetic resonance and combinations thereof. In one embodiment, the visualization agent can be one or more radiopaque elements or fillers which impart radiopacity to the devices described herein. In another embodiment, the visualization agent can be a non-radioapque element or filler such as gadolinium or iron oxide. Such non-radiopaque elements or fillers do not impart radiopacity to the devices described herein and can be imaged by, for example, magnetic resonance.

"Radiopaque" as used herein refers to elements or fillers as described above that impart radiopacity to the devices described herein and are detectable by a means of electrometric radiation such as, but not limited to, x-rays, ultrasound, fluoroscopy, infrared, ultraviolet and combinations thereof. In one embodiment, radiopaque elements described herein are detectable using x-rays or x-ray fluoroscopy.

The ionizable ethylenically unsaturated monomer serves to delay the expansion of the hydrogel filament, thereby establishing a controlled rate of expansion. In one embodiment, at least a portion, preferably about 5% to about 50% w/w of the monomer solution, more preferably about 5% to about 25% w/w of the prepolymer solution, of the monomers selected are ionizable. The preferred ionizable monomers may be acrylic acid or methacrylic acid. Derivatives and salts of both acids are also suitable ionizable components.

Alternatively, in one embodiment, ionizable ethylenically unsaturated monomers are not utilized.

In one embodiment optional ethylenically unsaturated monomers with a visualization agent that does or does not impart radiopacity to the devices are used to aid the polymerization process and can be any mono or multifunctional ethylenically unsaturated compound. In one embodiment, ethylenically unsaturated monomers with visualization agents without radiopacity with low molecular weights are preferred. Hydroxyethyl methacrylate (e.g. 2-hydroxyetyl methacrylate), hydroxyethyl acrylate, N-vinyl pyrrolidinone and N, N'-methylenebisacrylamide are preferred ethylenically unsaturated monomers visualization agents without radiopacity. Preferred concentrations of the ethylenically unsaturated monomers visualization agents without radiopacity are less than about 5% w/w, more preferably less than about 1% w/w of the prepolymer solution.

In one embodiment, the hydrogels and devices described herein further comprise visualization agents, such as, gadolinium or iron oxide in addition to radiopaque elements to impart visibility of the devices under magnetic resonance imaging. In other embodiments, the gadolinium or iron oxide are used instead of or in place of the radiopaque elements.

The optional porosigen serves to impart pores in the resulting polymer. The porosity of the hydrogel material is imparted as a result of a supersaturated suspension of a porosigen in the prepolymer solution. A porosigen that is not soluble in the prepolymer solution, but is soluble in the washing solution, can also be used. In one embodiment, sodium chloride is the preferred porosigen. In other embodiments, ice, sucrose, and sodium bicarbonate can also be used as porosigens. It is preferred that the particle size of the porosigen be less than about 25 microns, more preferably less than about 10 microns. The small particle sizes aid the suspension of the porosigen in the solvent. Preferred concentrations of the porosigen are less than about 50% w/w, more preferably less than about 20% w/w of the prepolymer solution. In some embodiments according to the present description a porosigen is not utilized.

The prepolymer solution can be cross-linked by reduction-oxidation, radiation, heat, or any other method known in the art. Radiation cross-linking of the prepolymer solution can be achieved with ultraviolet light or visible light with suitable initiators or ionizing radiation (e.g. electron beam or gamma ray) without initiators. Cross-linking can be achieved by application of heat, either by conventionally heating the solution using a heat source such as a heating well, or by application of infrared light to the prepolymer solution.

In a preferred embodiment, the cross-linking method utilizes azobisisobutyronitrile (AIBN) or another water soluble AIBN derivative (2,2'-azobis(2-methylpropionamidine) dihydrochloride). Other cross-linking agents useful according to the present description include N,N,N',N'-tetramethylethylenediamine, ammonium persulfate, benzoyl peroxides, and combinations thereof, including azobisisobutyronitriles. In one embodiment, the AIBN or derivative thereof is used at an elevated temperature. After addition of AIBN, the prepolymer solution is injected into poly(ethylene) tubing with an inner diameter ranging from 0.012 inches to 0.075 inches and incubated for several hours at 80° C. The selection of the poly(ethylene) tubing imparts microcatheter or catheter compatibility. For delivery through microcatheters, poly(ethylene) tubing diameters from about 0.012 inches to about 0.025 inches are preferred. For delivery through 5 French Size (Fr) catheters, poly(ethylene) tubing diameters from about 0.030 inches to about 0.050 inches are preferred. Alternatively, HYTREL® (DuPont, Wilmington, Del.) tubing of the same diameter can be utilized. The HYTREL® tubing can be dissolved in solvents, facilitating removal of the polymer from the tubing.

If the poly(ethylene) tubing is wrapped around a mandrel prior to polymerization of the prepolymer solution, the resulting polymer will maintain the shape of the poly (ethylene) or HYTREL® tubing, primarily as a result of the shapeable macromer within the prepolymer solution. Using this technique, helical, tornado, and complex shapes can be imparted to the polymer. The memory of the imparted shape is strongly influenced by the macromer selection. More hydrophobic macromers retain their imparted shape better than more hydrophilic macromers. It is preferred that an ethylenically unsaturated shapeable macromer be used in this embodiment.

In one embodiment, the devices described herein are environmentally responsive. Environmentally responsive as used herein means that the devices change in some way in response to the surrounding environment. In one embodiment, this response to the surrounding environment is in the form of a controlled rate of expansion. A controlled rate of expansion of the hydrogels described herein is achieved through the protonation/deprotonation of ionizable functional groups present within or on the hydrogel network. Once the hydrogel has been prepared and the unincorporated macromers, monomers, and oligomers have been washed away, the steps to control the rate of expansion can be performed.

If monomers with carboxylic acid groups are incorporated into the hydrogel network, the hydrogel is incubated in a low pH solution. The free protons in the solution protonate the carboxylic acid groups within the hydrogel network. The length of incubation, temperature during incubation, and pH of the solution influence the amount of control on the expansion rate. Generally, the length and temperature of the incubation are directly proportional to the amount of expansion control, while solution pH is inversely proportional. Surprisingly, it was found that the water content of the treating solution also affects the expansion control. As the water content increases, the hydrogel is able to expand more in the treating solution and it is presumed that an increased number of carboxylic acid groups are available for protonation. An optimization of water content and pH can be required for maximum control of the expansion rate. After the incubation is concluded, the excess treating solution is washed away and the hydrogel material is dried. It has been observed that hydrogel treated with the low pH solution dries down to a smaller dimension than the untreated hydrogel. In one embodiment, smaller dimensioned hydrogels are utilized since delivery of these hydrogel materials through a microcatheter is desired.

In contrast, if pH sensitive monomers with amine groups are incorporated into or on the hydrogel network, the hydrogel is incubated in a high pH solution. Deprotonation occurs on the amine groups of the hydrogel network at high pH. The length of incubation, temperature during incubation, and pH of the solution influence the amount of control on the expansion rate. Generally, the length and temperature of the incubation and solution pH are directly proportional to the amount of expansion control. After the incubation is concluded, the excess treating solution is washed away and the hydrogel material is dried.

In some embodiments according to the present description, non-aqueous solvents are utilized. In such embodiments, monomers with protonated carboxylic acids (e.g., acrylic acid or methacrylic acid) can be used in place of their corresponding salts (e.g. sodium acrylate or sodium methacrylate). The use of these monomers in non-aqueous solvents obviates the need for subsequent treatment in low pH solutions.

After the cross-linked hydrogel has been washed, it is dried and a dried hydrogel filament is produced. The length can range from about 0.5 cm to about 100 cm and the diameter can range from about 0.010 inches to about 0.100 inches. In some embodiments, a pushable embolic device is required. In these instances, the dried hydrogel filament is loaded into introducer tubing, packaged, and sterilized. Upon receipt, the surgeon pushes the dried hydrogel filament into the microcatheter or catheter with a wire or other pusher. The dried hydrogel filament is then advanced down the microcatheter or catheter to the embolization site.

In one embodiment, the hydrogels described herein are substantially free of acrylamide. Consequently, the hydrogels substantially free of acrylamide have less than about 1% (w/w %) acrylamide per hydrogel mass. In other embodiments, the acrylamide is less than about 0.5% or less than about 0.01% of the hydrogel mass.

In other embodiments, the hydrogel is non-bioresorbable or substantially non-bioresorbable. A "non-bioresorbable" hydrogel as used herein is biocompatible and not subject to breakdown in vivo through the action of normal biochemical pathways. In one embodiment, the hydrogel is substantially non-bioresorbable and remains greater than 95% intact after 1 year of implantation. In other embodiments, the substantially non-bioresorbable hydrogel remains greater than 90% intact after 1 year.

In yet a further embodiment, the hydrogel is bioresorbable, meaning the hydrogel is biocompatible and is broken down in vivo through the action of normal biochemical pathways. In one embodiment, the hydrogel is bioresorbable and remains less than 5% intact after 1 year of implantation. In other embodiments, the hydrogel is bioresorbable and remains less than 5% intact after 2 years of implantation. In other embodiments, the hydrogel is bioresorbable and remains less than 5% intact after 5 years of implantation.

In another embodiment according to the present description, a retrievable embolic device is required. In these instances, a coupler is attached to a dried hydrogel filament by gluing, swaging, or other means known in the art. The coupler permits attachment to a delivery pusher. After attachment to the delivery pusher, the dried hydrogel filament/delivery pusher construct is packaged and sterilized. Upon receipt, a surgeon introduces the device into a microcatheter or catheter and advances it to the embolization site. The surgeon can retract and advance the device until it is positioned adequately. At this time, the surgeon can detach the dried hydrogel filament from the delivery pusher and remove the delivery pusher from the microcatheter or catheter.

In another embodiment, a fluid assisted injectable embolic device is used. In this case, a dried hydrogel filament is loaded into an introducer, packaged, and sterilized. Upon receipt, the surgeon injects the dried hydrogel filament into the microcatheter or catheter with a syringe filled with saline or other physiological solution. The saline or other physiological solution is used to assist in advancing the hydrogel filament down the catheter in addition to hydrating it. The dried hydrogel filament is then advanced down the microcatheter or catheter to the embolization site with subsequent injections.

EXAMPLES

The following are non-limiting examples of some of the biomedical applications of hydrogels with visualization agents described herein. It will be appreciated, however, that this material has many other medical and non-medical applications in addition to the specific examples set forth herein.

Example 1

Preparation of PEG 1000 Diacrylamide

First, 18 g of polyethylene glycol (PEG) 1000 was dried by azeotropic distillation with 200 mL of toluene. Then, 7.0 mL of triethylamine was added with 4.6 mL of mesyl chloride and stirred for 4 hr. The solution was then filtered to remove salt and the solvent evaporated. The resulting product was added to 150 mL of 25% ammonia hydroxide and stirred for 2 days. The water was removed and the product dried by azeotropic distillation with toluene. The resulting dried PEG diamine was dissolved in 20 mL dichloromethane and 50 mL toluene. Then, 7.0 mL of triethylamine and 4.9 mL of acryloyl chloride were added and the reaction proceeded for 4 hr while stirring. The resulting solution was filtered and the solvent was removed leaving PEG 1000 diacrylamide.

Example 2

Preparation of a Radiopaque Monomer

First, 9 g of triiodophenol was dissolved in 150 mL dichloromethane under argon. Then, 3.15 mL of pentenoyl chloride was added while stirring. Triethylamine was then added slowly and stirred for 4 hr. The solution was washed with 100 mL of water and evaporated to dryness, leaving 2,4,6-triiodophenyl penta-4-enoate.

Example 3

Preparation of a Radiopaque Hydrogel Filament in Chloroform

To prepare a radiopaque hydrogel in an organic solvent, 2 g of 2,4,6-triiodophenyl penta-4-enoate, 0.67 g of acrylic acid, 1.2 g of PEG diacrylamide 400, 24 mg of N,N-methylenebisacrylamide and 75 mg of azobis(2-methylpropionitrile) were dissolved in 2.5 mL of chloroform. Then, the solution was sparged with argon for 10 min before injection into a 0.020 inch polyethylene tubing using a 3 cc syringe. The tubes were heat sealed at both ends and placed in an 80° C. oven overnight to polymerize the solution.

Example 4

Preparation of a Barium Loaded Radiopaque Hydrogel Filament

To prepare a barium-loaded radiopaque hydrogel in an organic solvent, 7 g of barium sulfate, 0.5 g of acrylic acid, 5 g of poly(tetramethylene oxide) diacrylamide 1000, 1.25 g of 2-hydroxyethylemethacrylate, 212 mg of N,N-methylenebisacrylamide and 100 mg of azobis(2-methylpropionitrile) were dissolved in 3.5 mL of isopropyl alcohol. The solution was then sparged with argon for 10 min before injection into 0.010 inch HYTREL® tubing wrapped around a 4 mm mandrel using a 3 cc syringe. The tubes were heat sealed at both ends and placed in a 100° C. water bath for 1 hr, then overnight in an 80° C. oven to polymerize the solution.

Example 5

Preparation of a Radiopaque Hydrogel Filament in Water

To prepare a radiopaque hydrogel in water, 5 g of 2,5-acrylamido-2,4,6-triiodo-n,n'-bis-(2,3 dihydroxypropyl) isophthalamide, 1.33 g of acrylic acid, 2.5 g PEG diacrylamide 400, 50 mg of n-vinyl-2-pyrrolidinone and 100 mg of 2,2'azobis(2-methylpropionamidine) dihydrochloride were dissolved in 10 mL of water. The solution was then sparged with argon for 10 min before injection into 0.020 inch polyethylene tubing using a 3 cc syringe. The tubes were heat sealed at both ends and placed in an 80° C. oven overnight to polymerize the solution.

Example 6

Washing and Acid Treatment of a Radiopaque Hydrogel Filament

For the hydrogel polymerized according to Example 3, the tubes were cut into 3 inch sections and placed in acetone for 1 hr. In acetone, the hydrogel expanded out the ends of the tubes, allowing it to be removed from the tube. The hydrogel was washed in acetone for 2 hr. After 2 hr, the acetone was exchanged and the hydrogel was washed for another 2 hr. The acetone was removed and the hydrogel dried in a vacuum oven for 2 hr at 50° C.

For hydrogels polymerized according to Example 4, the hydrogel was removed by dissolving the tubing in a solution of 20% phenol in chloroform. After the tubing was dissolved, the phenol solution was exchanged with chloroform and washed for 1 hr. After 1 hr, the chloroform was exchanged and the hydrogel washed for another 1 hr. The chloroform was removed and the hydrogel dried in a vacuum oven for 2 hr at 50° C. To remove any unreacted monomers, the hydrogel was placed in ethanol for 12 hr. After 12 hr, the ethanol was exchanged and washed for 2 hr. After 2 hr, the ethanol was exchanged and the hydrogel washed for another 2 hr. The ethanol was removed and hydrogel dried in a vacuum oven for 12 hr.

For the hydrogel polymerized according to Example 5, the tubes were cut into 3 inch sections and placed in the vacuum oven for 6 hr at 50° C. Once the hydrogel was dried, it can be pushed out of the tubes using a mandrel. The hydrogel was washed in water for 2 hr. After 2 hr the water was exchanged and the hydrogel was washed for another 2 hr. The water was removed and the hydrogel dried in a vacuum oven for 2 hr at 50° C.

Acid treatment of the hydrogels consisted of incubating in 1N hydrochloric acid (HCl) for 4 hr at 37° C. After 4 hr the acid was decanted off. The hydrogel was incubated in 99% isopropyl alcohol for 1 hr to remove any remaining acid. The hydrogel was dried in a vacuum oven for 1 hr at 50° C. to remove the remaining isopropyl alcohol.

Example 7

Attachment of a Radiopaque Hydrogel Filament to a Pusher

The radiopaque hydrogel filament can be attached to a V-TRAK® (MicroVention Terumo, Inc., Aliso Viejo, Calif.) or hydraulic pusher. To attach the hydrogel to a V-TRAK® pusher, a section of 0.0022 inch poly(ethylene) tubing suture was threaded through a coupler. The coupler consisted of a titanium cylinder hollowed out on one end and a through hole. The poly(ethylene) tubing suture was tied into a knot such that it could not be pulled back through. The hydrogel was glued into the coupler on top of the knot using adhesive. The other end of the poly(ethylene) tubing thread was threaded into a V-TRAK® pusher and tied.

To attach the hydrogel to a hydraulic pusher, a bullet coupler was used. The gel was glued into the coupler using adhesive and attached to a hydraulic pusher using heat shrink PET tubing.

Example 8

Measurement of Buckling Force

To compare the ability of the radiopaque hydrogel filament of Example 6 to deploy inside aneurysm sacs with other currently marketed coils, the buckling force of a variety of devices was determined. In this test, approximately one inch pieces of the devices were attached to about 15 inch pieces of hypo tubing by either soldering or poly (ethylene) shrink tubing. The hypo tubing end of the constructs was attached to an Instron 5543 Single Column Testing System, a system used to measure force data of materials. The construct was advanced down a dead end channel in a poly(carbonate) block. When the device reached the bottom of the channel, it was forced to buckle and the corresponding force was measured.

| Group | Buckling Force (gf) |
|---|---|
| HYPERSOFT ® Platinum Coil (MicroVention Terumo, Inc., Aliso Viejo, CA) | 0.6 ± 0.4 |
| MICROPLEX ® Platinum Coil 0.010 inch (MicroVention Terumo, Inc., Aliso Viejo, CA) | 2.3 ± 1.0 |
| HYDROCOIL ® 10 (MicroVention Terumo, Inc., Aliso Viejo, CA) | 11 ± 4 |
| Radiopaque Hydrogel Filament | 0.5 ± 0.4 |

Three types of currently marketed coil systems were tested and compared to the radiopaque hydrogel filament of Example 6. The first coil tested was a HYPERSOFT® Platinum Coil. The HYPERSOFT® Platinum coil is a soft platinum finishing coil with an outer diameter of 0.012 inch and a filar size of 0.002 inch. The second coil tested was a MICROPLEX® Platinum Coil. The MICROPLEX® Platinum coil is a platinum filling coil with an outer diameter of 0.010 inch and a filar size of 0.002 inch. The HYPERSOFT® Platiumun coil and MICROPLEX® Platinum coil are soft platinum helical coils with no expandable hydrogel. The third coil tested was a HYDROCOIL® 10 system. The HYDROCOIL® 10 system is a platinum coil with an outer diameter of 0.008 inch and a filar size of 0.002 inch jacketed with an expandable poly (acrylamide-co-acrylic acid) hydrogel and overcoiled with a stretched platinum coil. Statistically significant differences in the buckling force of the radiopaque hydrogel filament and the HYPERSOFT® Platiumun coil, an extremely soft platinum coil, were not observed. This experiment demonstrated that the radiopaque hydrogel filament has soft deployment characteristics suitable for embolic devices.

Example 9

Measurement of Bending Resistance

The bending resistance of the unexpanded hydrogel samples and the bending resistance of injectable platinum microcoils were obtained using a Gurley 4171ET tubular sample stiffness tester with a 5 g counterweight attached to its measuring vane. The sample length was one inch. The average of three replicates each are summarized in the following table.

| Sample | Measured Resistance (mg) |
|---|---|
| D-51 radiopaque hydrogel filament | 0.9 ± 0.4 |
| 0.008 inch platinum microcoil | 0.6 ± 0.2 |

The results illustrate little difference in relative stiffness between the radiopaque hydrogel filament and the platinum microcoil. The results demonstrate that the flexibility of an injectable platinum coil can be achieved with a radiopaque hydrogel filament.

Example 10

Evaluation of an Injectable Radiopaque Hydrogel Filament

Devices constructed from barium loaded radiopaque hydrogel formulations were evaluated in a flow model fitted with a torturous vessel. A flow directed microcatheter (Boston Scientific Spinnaker 1.5 F) was placed in the vessel. Devices ranging from 5 cm to 30 cm in length were injected through the microcatheter using a 3 cc syringe. The devices were evaluated on introduction, tracking, deployment and packing. To achieve a pass for Intro, Tracking, and Deploy, the implant must introduce, track and deploy using a 3 cc syringe without incident. To achieve a pass for packing, the implant must pack in a torturous vessel similar to a 0.008 inch platinum coil.

| Formulation | Intro | Tracking | Deploy | Packing |
|---|---|---|---|---|
| D-51 radiopaque hydrogel filament | Pass | Pass | Pass | Pass |
| 0.008 inch platinum coil | Pass | Pass | Pass | Pass |

The results illustrate that the radiopaque hydrogel filaments can be deployed into a simulated use torturous path and perform consistent with other embolic devices such as platinum coils.

Example 11

Evaluation of Radiopaque Polymer Hydrogel in Experimental Aneurysms

Three rabbit elastase aneurysms were embolized with radiopaque polymer filaments. The aneurysm width, length, and neck ranged from 2.4 to 3.6 mm, 4.7 to 8.8 mm, and 2.4 to 4.2 mm, respectively. A microcatheter (Cordis RAPIDTRANSIT®, Cordis Corporation, Miami Lake, Fla.) was placed inside the aneurysm sac. One to three radiopaque hydrogel filaments were deployed inside the aneurysm sac. Angiography demonstrated complete occlusion of all three aneurysms as a result of the embolization. At 6 wk post-embolization, complete occlusion of all three aneurysms was demonstrated by angiography. The aneurysms were harvested and histologically processed. The sections demonstrated complete filling of the aneurysm sac with the radiopaque hydrogel filaments, organizing/organized fibrous tissue in the clefts between the radiopaque hydrogel filaments, and an inflammatory response consisting of macrophages and a few giant cells. These results illustrated that the radiopaque hydrogel filaments can be deployed into experimental aneurysms and elicit a foreign body response consistent with other embolic devices.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments of this invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Furthermore, numerous references have been made to patents and printed publications throughout this specification. Each of the above-cited references and printed publications are individually incorporated herein by reference in their entirety.

In closing, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

Specific embodiments disclosed herein may be further limited in the claims using consisting of or and consisting essentially of language. When used in the claims, whether as filed or added per amendment, the transition term "consisting of" excludes any element, step, or ingredient not specified in the claims. The transition term "consisting essentially of" limits the scope of a claim to the specified materials or steps and those that do not materially affect the basic and novel characteristic(s). Embodiments of the invention so claimed are inherently or expressly described and enabled herein.

We claim:

1. A device for implantation comprising:
   a hydrogel filament attached to a coupler wherein the coupler is attached to a pusher,
   wherein the hydrogel filament includes a low molecular weight ethylenically unsaturated macromer; an ethylenically unsaturated monomer; and visualization agent having a structure of 2,4,6-triiodophenyl penta-4-enoate,
   wherein said device contains no support members.

2. The device of claim 1, wherein said macromer has a molecular weight of about 100 grams/mole to about 5000 grams/mole.

3. The device of claim 1, wherein said macromer comprises polyethylene glycol, propylene glycol, poly(tetramethylene oxide), poly(ethylene glycol) diacrylamide, poly(ethylene glycol) diacrylate, poly(ethylene glycol) di methacrylate, derivatives thereof, or combinations thereof.

4. The device of claim 1, wherein said macromer and said monomer are crosslinked with N,N,N',N'-tetramethylethylenediamine, ammonium persulfate, azobisisobutyronitrile, benzoyl peroxides, 2,2'-azobis(2-methylpropionamidine) dihydrochloride, derivatives thereof, or combinations thereof.

5. The device of claim 1, wherein said hydrogel is substantially free of acrylamide.

6. The device of claim 1, wherein said hydrogel is substantially non-bioresorbable.

7. The device of claim 1, wherein said visualization agent is at a concentration of about 40% w/w to about 80% w/w of a prepolymer solution used to form the hydrogel filament.

8. A device for implantation comprising:
   an introducer loaded with a hydrogel filament, wherein the introducer attaches to a catheter or microcatheter,
   wherein the hydrogel filament includes a low molecular weight ethylenically unsaturated macromer; an ethylenically unsaturated monomer; and visualization agent having a structure of 2,4,6-triiodophenyl penta-4-enoate,
   wherein said device contains no support members.

9. The device of claim 8, wherein said macromer has a molecular weight of about 100 grams/mole to about 5000 grams/mole.

10. The device of claim 8, wherein said macromer comprises polyethylene glycol, propylene glycol, poly(tetramethylene oxide), poly(ethylene glycol) diacrylamide, poly(ethylene glycol) diacrylate, poly(ethylene glycol) di methacrylate, derivatives thereof, or combinations thereof.

11. The device of claim 8, wherein said macromer and said monomer are crosslinked with N,N,N',N'-tetramethylethylenediamine, ammonium persulfate, azobisisobutyronitrile, benzoyl peroxides, 2,2'-azobis(2-methylpropionamidine) dihydrochloride, derivatives thereof, or combinations thereof.

12. The device of claim 8, wherein said hydrogel is substantially free of acrylamide.

13. The device of claim 8, wherein said hydrogel is substantially non-bioresorbable.

14. The device of claim 8, wherein said visualization agent is at a concentration of about 40% w/w to about 80% w/w of a prepolymer solution used to form the hydrogel filament.

* * * * *